United States Patent
Mochnal et al.

Patent Number: 5,681,709
Date of Patent: Oct. 28, 1997

[54] AUTOMATED PROCESS FOR PREPARING TREATED MICROPARTICLES ESPECIALLY BLOOD CELL COMPONENTS

[75] Inventors: Dennis Mochnal, Clinton; Janice Jakway, Bridgewater, both of N.J.; Gilbert J. Quinton, Staten Island, N.Y.

[73] Assignee: Ortho Diagnostic Systems Inc., Raritan, N.J.

[21] Appl. No.: 375,082

[22] Filed: Jan. 17, 1995

Related U.S. Application Data

[63] Continuation of Ser. No. 200,903, Feb. 23, 1994, abandoned, which is a continuation of Ser. No. 700,688, May 15, 1991, abandoned.

[51] Int. Cl.$^6$ .................................................. G01N 33/49
[52] U.S. Cl. ...................... 435/7.25; 435/240.1; 435/2; 436/174; 424/93.73; 424/533
[58] Field of Search .......................... 422/44; 435/2, 435/7.25, 240.1; 436/177, 178, 8, 174; 424/533, 93.73

[56] References Cited

U.S. PATENT DOCUMENTS

| | | |
|---|---|---|
| 3,737,096 | 6/1973 | Jones et al. ............... 233/19 A |
| 4,107,287 | 8/1978 | Morton et al. . |
| 4,306,556 | 12/1981 | Zelman ..................... 128/272 |
| 4,804,363 | 2/1989 | Valeri ........................ 604/6 |
| 4,839,058 | 6/1989 | Cawley et al. .............. 210/670 |

OTHER PUBLICATIONS

Andersson, T.R. "Preparation of Antibody–Coated red cells by the Haemonetics Cell Separator or Cell Washer" 1979 Vox Sang, 36:312.

*Primary Examiner*—Paula K. Hutzell
*Assistant Examiner*—Rachel Heather Freed

[57] ABSTRACT

A method for preparing treated naturally occurring or synthetic particles using a blood cell processor is provided. The method comprises adjusting the blood cell processor to allow a dispersion of such particles to come into contact with a treatment material in an amount and for a period of time sufficient to modify all or a portion of the surface of such particles. In a preferred embodiment, the method comprises washing collected red blood cells; separating a selected volume of said washed red blood cells; and treating one portion of said separated washed cells with a selected proteolytic enzyme, to prepare a red blood cell reagent.

6 Claims, 1 Drawing Sheet

AUTOMATED PROCESS FOR PREPARING TREATED MICROPARTICLES ESPECIALLY BLOOD CELL COMPONENTS

This is a continuation of application Ser. No. 08/200,903 filed on Feb. 23, 1994 (abandoned) which is a continuation of Ser. No. 07/700,688 filed on May 15, 1991 entitled AUTOMATED PROCESS FOR PREPARING TREATED MICROPARTICLES, ESPECIALLY BLOOD CELL COMPONENTS (abandoned).

BACKGROUND OF THE INVENTION

There exists many naturally occurring or synthetic particles such as blood cell components, cell membrane fragments, latex or polystyrene beads of various sizes, other microspheres the size of blood cells, liposomes, and the like, that are useful in immunochemistry, agglutination procedures, and other similar assays, especially in the field of diagnostic reagents. In many instances it is necessary to wash, coat, or otherwise treat and modify the surface of such particles prior to use or prior to packaging in a commercial reagent. For example, flow microsphere-based immunoassays (FMIA) known to the art detect and quantitate specific antibodies using antigen coated microspheres. Immunochemica, Volume 5, Number 1, January 1991, a publication by Zymed Laboratories, San Francisco, Calif. Accordingly, there exists in the art a need to handle the treating of such particles in a manner that is so economic, timely, and reliable as to render a commercially viable treatment process.

Blood cell components form a major class of naturally-occurring particles. Blood cell components from a patient are frequently the subject matter of diagnostic testing, or are the basic components of a blood cell diagnostic reagent. For example, the field of blood group serology requires the determination of blood cell compatibility between donor and patient before a transfusion or organ transplant. Blood cell compatibility is determined by the non-occurrence of an immunological reaction between antibodies contained in the blood serum of a patient and antigens present on blood cells from a donor. A patient whose red blood cells are Type A, i.e., having "A" antigens on the red cells, will have Anti-B antibodies in his or her serum. Thus, if such a person is given type B blood, an immunological reaction will occur with possible serious clinical consequences.

Tests for blood cell typing and compatibility are generally of two types: (1) agglutination tests which determine whether a specific antibody added to the cells will cause their agglutination, and (2) cell lysis tests which determine whether a specific antibody added to the tested cells together with serum complement results in hemolysis.

In blood cell typing and compatibility test procedures commonly used, both agglutination and cell lysis tests are carried out either manually by a trained technician or using sophisticated automated devices. However, these tests may not be sensitive enough to detect weakly reacting antibodies or to differentiate complex mixtures of antibodies.

Enzymes are catalytic proteins which accelerate certain biological reactions. In immunohematology, proteolytic enzymes such as ficin, bromelin, papain, and trypsin remove sialic acid from the red cell surface. Enhanced red cell agglutination may be observed after enzyme treatment due to the exposure of latent antigen sites. In addition, the surface charge of the red cell is reduced, decreasing cell-cell repulsion. Certain other antigen-antibody reactions may be depressed or eliminated, due to the removal of some antigen sites after enzyme treatment.

Enzymes can be used in two different ways in blood group serology. An enzyme solution can be added directly to a serum-cell mixture (one stage method), or the red cells can be pretreated with enzyme before serum is added (two stage method). The one stage method is faster and more convenient, but is not as sensitive as the two stage method. An advantage of the latter is better modification of the red cell membrane due to the absence of serum proteins. Accordingly, there exists in the art a need for a faster, more accurate method of commercially preparing enzyme treated cells for use as reagents in blood analysis techniques.

Additionally, other types of treatment of blood components may be desirable. For example, blood is generally treated with a solution to protect the cell membranes and their components prior to freezing. In some instances, it may be desirable to treat large quantities of blood on a continuous basis. It may also be useful to treat other blood components, such as white blood cells, platelets and the like with fixative solutions, preservation solutions, and other similar types of treatment.

Automated blood cell processors are known to the clinical art as automated blood component processing devices. These are generally used in hospital and other clinical settings to purify blood components by eliminating the majority of unwanted formed elements of blood, debris and fluids. Plasma, red cells, white cells, and platelets may be separated and discarded, or harvested for use. Blood components are separated by centrifugation, and cleansed through mixing and dilution with saline and other red cell washing solutions.

SUMMARY OF THE INVENTION

The present invention relates to a method of treating particles dispersed in a medium, using a blood cell processor. The present method is particularly suitable for treating naturally-occurring particles, such as blood cell components. In particular, a method for the preparation of enzyme-treated red blood cells is disclosed. The resulting enzyme-treated red cells are useful for selecting compatible blood for patient transfusion.

The method of the invention comprises using a blood cell processor to treat selected particles disposed in a medium, and prior to or following such treatment, to optionally wash and/or separate a selected volume of such particles.

In preferred embodiments, a blood cell processor is used to wash such particles; to separate a selected volume of said particles; and to treat one or more portions said separated washed particles with a selected treatment material. The treated particle suspension may be further washed and diluted prior to use. In particularly preferred embodiments, a blood cell processor is used to wash a collected volume of blood cells, to separate such volume into two or more parts, and to treat one or more parts of such separated volumes with a proteolytic enzyme.

An automated blood component processing device may be used manually or electronically programmed to add and mix the particles with an appropriate gaseous or liquid solution containing the treatment material and optionally various wash solutions in a specified manner. In the preferred embodiments, the particles are red blood cells and the treatment material is a proteolytic enzyme solution.

DETAILED DESCRIPTION OF THE INVENTION

Figure 1:
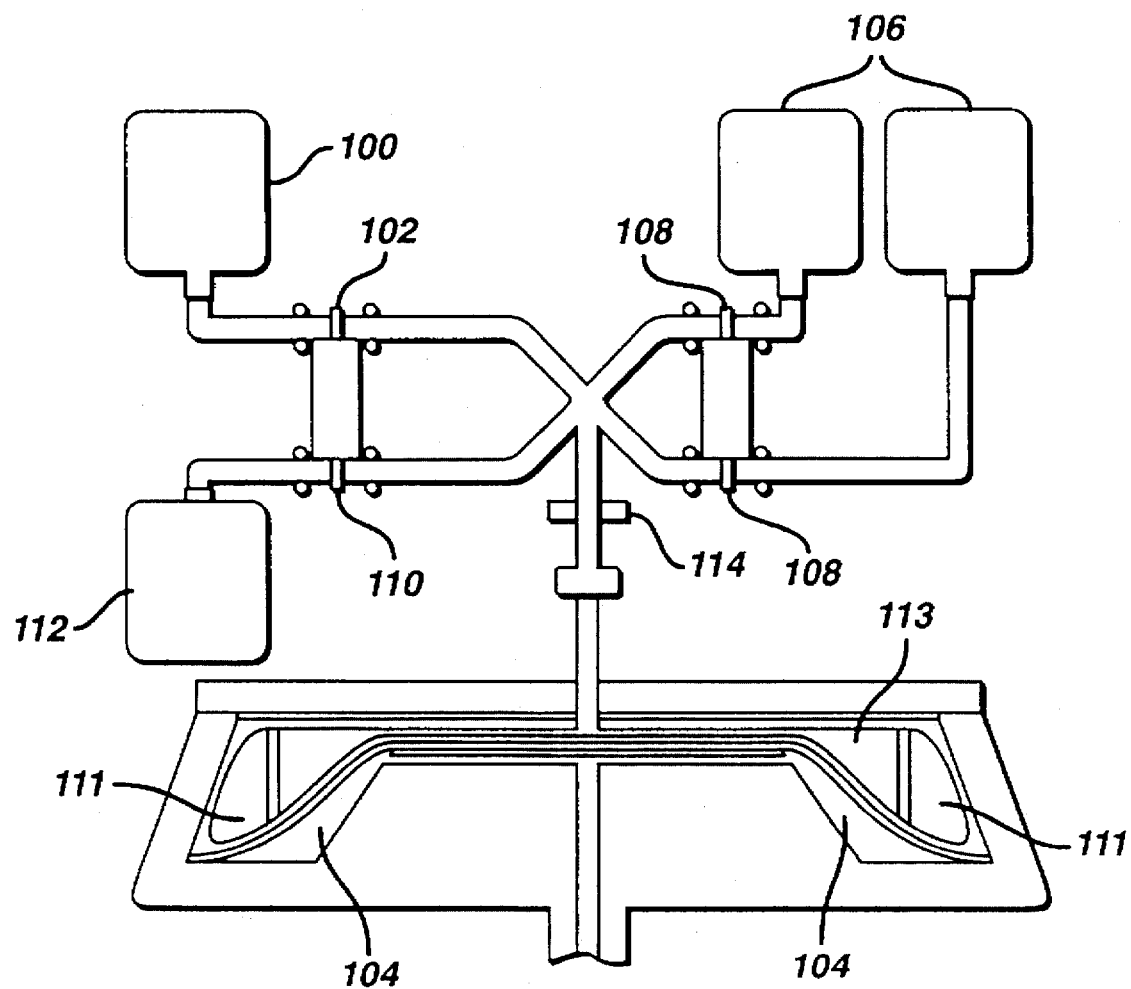
FIG. 1 is a block diagram of a COBE 2991 Blood Cell Processor.

In the present invention, treatment of particles, and in particular, naturally occurring particles such as red blood cells, with one or more specified treatment materials has been greatly automated, resulting in the enhanced ability of the user to easily and economically prepare a quantity of treated particles. Such particles may be suitable for use in a biological reagent. Red blood cells treated in accordance with the present invention may be used in a diagnostic reagent that demonstrates excellent stability, accuracy, and sensitivity.

In the method of the invention, an automated blood component processing device may be directed manually by the user or may be electronically programmed using conventional random logic controls, often provided commercially as part of the equipment, to add and mix the particles dispersed in a carrier medium with the selected treatment material. The instrument may operate in a continuous flow manner, or on the basis of a batch method. These blood cell processors have been known to the art for the washing of red cells, such as in washing frozen blood units prior to use. The equipment provides means for adding blood units to a "bowl" area, that acts as a centrifuge. In some respects, the instrument setup resembles the common laundry washing machine.

Means to add solutions, means of agitating the particle dispersion added, (along with the solutions if desired), means for expressing out solutions and/or particle dispersions, thereby separating such units, are critical features of these devices that render the presently claimed method superior to the art-accepted treatment of particles to coat them or modify their surface properties, and so on. For example, a generally accepted method of treating red blood cells with a proteolytic enzyme to modify the blood cell surface antigen is to accomplish this by manual handling of the blood unit. The presently claimed process offers a superior alternative to this accepted technique. In particularly preferred embodiments, means of incubating the particle dispersions and/or various solutions is also provided.

In its broadest aspect, the method of the invention comprises one or more of the following steps, using a blood cell processor. A particle dispersion is washed or otherwise contacted with a wash solution in a blood cell processor with specified settings. A selected volume of the particle dispersion may also be separated into two or more parts, with one or more of the parts treated in the same manner or differently than the other separated parts. For example, one or more of the separated parts may be treated with a treatment material, while other separated parts are not. Or, the separated parts may be treated in sequential fashion with the same treatment material, or individual separated parts may be treated with differing treatment materials. Additional washing and/or dilution steps may also be included. The resulting treated particles can then be further processed for ultimate use, or, are ready to be used diagnostically, for example, in prepared red cell reagents, latex bead reagents, polystyrene bead reagents, magnetic bead reagents, liposome reagents, and the like.

Suitable blood cell processors for use herein will provide great flexibility, reliability, and accuracy in the separation and treatment of a particle dispersion. Blood cell processors suitable for use herein will provide great flexibility in the adding of various solutions at various time periods, agitating such solutions and particle dispersions, and expressing off waste after such addition and agitation. For example, in the preferred embodiments as described below, once a separated portion of a blood product unit has been treated with an enzyme solution in accordance with the method provided herein, the cell processor can be directed to "wash off" excess enzyme, thereby avoiding any contamination or deleterious effect such excess may have on the portion so treated, rendering a useful and stable reagent.

Blood cell processors useful in the method of the invention may be obtained commercially. For example, a cell washer, is available from Baxter Travenol of McGaw, Ill.; Haemonetics 15 Cell Washer System® is available from Haemonetics of Braintree, Mass.; the Cobe 2991 Blood Cell Processor® is available in the United States from COBE Laboratories, Inc. of Lakewood, Colo., and internationally from many other COBE affiliates. One skilled in the art of such instrumentation may also devise their own instrument set up, capable of performing the steps and meeting the criteria as described throughout this specification. Preferred for use herein is the COBE 2991 model as described above.

As used herein, a "particle dispersion" refers to naturally occurring or synthetic particles dispersed, dissolved, suspended, or the like in a medium that is compatible, such as water, physiological buffers, naturally occurring plasma, organic solvents, organic or inorganic solutions, and the like. This particle dispersion is of such a nature that it may be metered through a tube or other appropriate linefeed contained on the blood cell processor, as for example those leading into and away from the bowl area of the cell processor. Accordingly, the dispersion should be of a viscosity that will not impede its flow too greatly, and somewhat mimics the viscosity of a unit of blood (defined below).

By naturally occurring particles is meant particles such as bacterial, viral and other biological particles, cell membrane fragments, formal elements of blood such as red blood cells, white blood cells, platelets, reticulocytes, and the like. By synthetic particles is meant those particles of such a size that they would ultimately be suitable for use as solid supports, labels, or other components in biological assay formats, such as for example, microspheres such as latex beads, magnetic beads, polymethacrylate microspheres, liposomes, polystyrene beads, glass beads, and the like. The particles may be treated in accordance with the invention at any stage in their overall processing. For example, they could already be coated particles, wherein the coating has been carried out through another technique. These pre-coated particles could then be further treated in accordance with the present process.

By a "wash solution" is meant any medium, gaseous or liquid, that would not contain a treatment material (as hereinafter defined) but would be contacted with the particle dispersion to remove unwanted debris and other components, would wet the particles, would penetrate into the particles, dilute the particle treatment material, and the like.

By "treatment material" is meant that material whether in gaseous form or liquid form of suitable viscosity and/or of a granular nature or not, useful in treating particles in accordance with the invention to coat them, activate them, or otherwise modify them in some way. For example, the particles may be treated with a suitable treatment medium so as to charge their surface or change their surface charge, and thereby activate them for further processing such as subsequent ionic or covalent linkages with other substances. Additionally, the particles may be coated with various organic, inorganic, biological agents, and the like, such as albumin, gelatin, blood sera from various sources, nucleotides, antibodies, photofluorescent compounds, sugars, dyes of all kinds such as phycobiliproteins, rhodamine, fluorescein, stilbene, and the like, and, enzymes, bacterial or viral components, and the like. Additionally, the surface properties of the particles may be modified by contact with a material that will strip or modify surface antigens, or by contact with chemicals or gas resulting in sulfonation, amination, hydrolysis, oxidation, and the like.

Particularly useful for treatment in accordance with the method described herein are blood cell components of all kinds, and particularly a "blood product". As used herein, the term "blood product" means any product containing red blood cells in whole or any portion thereof, that one desires to separate into select quantities and to treat with a treatment material. Particularly suitable for the treatment provided herein are units of blood, whether provided as "whole" or as "packed red cells". A "unit of blood" is the term generally ascribed by those skilled in the art as a volume of blood drawn from a donor containing red cells and plasma and an anticoagulant to prevent clotting, and typically ranges in volume from about 400 ml to about 500 ml for adult units and about 100 mls to about 200 mls for low volume units. "Packed red cells" refers to those units wherein plasma is removed, typically in the range of about 20%–40% by volume.

In the preferred embodiments of the present method, the blood cell processor is capable, upon direction by the user, of separating a unit of blood product into approximately equal quantities, most preferably into two parts, each resulting in quantities between about 45% and 55% of the starting quantity. Although the preferred method requires that the blood be separated into two parts of approximately equal size, one skilled in the art will understand that the volume ratio that a particular unit of blood product could be separated into could vary tremendously, as could the number of parts the unit is separated into. One skilled in the art will further understand that the number of units and volume ratios will depend on the intended treatment of each of the parts the unit is broken down into, as well as the intended use of the parts or resulting reagent, after treatment.

In these preferred embodiments, the treatment material is a proteolytic enzyme such as bromelin, papain, trypsin, and ficin, with the latter particularly preferred. The ficin treated red blood cells in accordance with a preferred embodiment of the invention, are useful in the production of a ficin blood cell reagent panel, such as that sold by Ortho Diagnostic Systems Inc., under the tradename Resolve Panel C®. The preferred method of the invention has been optimized to direct the blood cell processor to treat approximately one half of a blood unit with ficin, resulting in an accurate and reliable equal quantity of treated and non-treated red blood cells ultimately provided in the aforementioned commercially available reagent kit.

Certain method steps of the invention will be described in more detail by referring to the preferred embodiment of treating red blood cells with an enzyme solution. When an unexpected antibody has been detected in serum it must be identified to determine its clinical significance. In some instances, such as when multiple antibody specificities of weak reactivities occur, it may be necessary to employ further test methods to recognize the antibody specificity (ies). The use of enzyme-treated red cells is one of the primary means by which antibody differentiation and recognition can be accomplished in these situations.

Proteolytic enzymes such as ficin, bromelin, papain and trypsin modify red cell antigens in ways that enhance the reactivity of some antigen/antibody reactions and destroy or alter antigenic determinants of others.

Following enzyme treatment of red cells, some antigens are destroyed or altered such as M, N, $Fy^a$, $F^b$, S, s, $Xg^a$, Pr, $Ch^a$, $Rg^a$ and $Yk^a$. The reactivity of most examples of antibodies directed against these antigens will be eliminated or reduced.

Enzyme modification of red blood cells can increase the reactivity of some antibodies with their corresponding antigens such as Rh, Kidd, Lewis, Vel and I. The exact mechanism by which antibody enhancement occurs is unknown. It has been suggested that the mechanism may involve either exposure of latent antigen sites on the red cell surface or that the removal of peptide chains reduces the net negative charge of the red cell allowing agglutination to occur.

Referring now to FIG. I, a blood product is added to the COBE Blood Cell Processor depicted therein at the blood product receptacle, 100. A suitable tube allows the blood product to feed down through the pinch valve 102 and into the centrifuge bowl 104. In a similar manner, a wash solution is provided at the wash solution receptacle, 106 and allowed to feed through an appropriate tube through the wash solution pinch valve 108 into the centrifuge bowl 104. Suitable tubing for the controlled addition of these components may be selection from polypropylene tubing, polyvinyl tubing, Teflon® tubing, siliconized tubing, and the like. Suitable wash solutions for this portion of the method are those compatible with red blood cells, and facilitate the washing of debris and other undesirable blood components while preserving the red blood cell membranes intact. These buffers include phosphate buffered saline, Alsevers Solution, physiological saline, Hanks Balanced Salt Solution, Ortho Resuspension Solution® available from Ortho Diagnostic Systems Inc., combination Alsevers and ethylenediamamine tetraacetic acid, and the like. After the blood product and the wash solutions are added to the centrifuge bowl, the bowl is agitated to mix the contents and allow adequate contact of the wash solution with the blood product. The contents are then centrifuged, allowing the red cells to pack around the perimeter of the bowl, 111. Excess wash solution containing the undesired waste components, 113, leaves through an appropriate line via the waste collect pinch valve 110 into a waste collecting receptacle 112, or other suitable means for a container or continuous egress. During the centrifugation process, the waste line opens to allow the egress of the waste fluid, as a diaphragm (not pictured) moves up through the centrifuge bowl to push the fluid up and out. A red cell detector 114 forces the line of egress closed when all the solution is expressed and red cells are starting to be forced up into the waste line. At this point, the centrifugation is halted, and the wash line allowed to add more wash solution for resuspension of the red cells and a repeat of this washing process. This is allowed to repeat as many times as the user desires to ensure adequate removal of unwanted components from the blood product. In the preferred ficin treatment method of the invention, this washing procedure is preferably repeated for a total of three times. The instrument is then adjusted manually, or programmed to allow approximately one-half of this thoroughly washed unit to exit via a fourth, separation line, through a separation pinch valve, and into a clean container (all not pictured on the cell processor in FIG. 1). This clean container may also comprise a separate bulk unit useful in collecting huge quantities of separated blood product units for further processing and packaging for commercial reagent. The portion of the blood product still remaining in the centrifuge bowl is washed one additional time, with excess wash solution expressed almost completely, and the remaining red blood cells packed once again.

One skilled in the art will appreciate that treatment of blood product with proteolytic enzymes is a very delicate process that must employ a balance of buffers and the like. Accordingly, use of the blood cell processing instrument as provided herein affords the opportunity to carefully and adequately wash the blood product and to ensure that no excess wash remains that could possibly interfere with subsequent treatment of the blood product. A proteolytic enzyme solution is then added in the same manner as the original blood product had been added, through blood product receptacle 100, and so forth. Suitable enzymes for treatment of the blood product in accordance with the methods taught herein are papain, bromelin, trypsin, ficin, and the like, in a suitable solution that preserves the activity and stability of the enzyme such as phosphate buffered solution with or without EDTA. Particularly preferred is a ficin treatment with ficin provided in a phosphate/Ortho Resuspension Solution® solution at a diluted concentration of about 0.02% to about 0.25%, and more preferably about 0.05 to 0.1%. One skilled in the art will understand that the enzyme solution must be compatible with the wash solutions, and at a concentration that has been optimized with respect to time, temperature, and other assay parameters. In the preferred ficin treatment embodiments, the treatment is conducted at ambient temperature by allowing contact and agitation of the blood product with the enzyme solution for a period of time that allows optimal enzyme-substrate interactions, generally about 2 minutes to about 30 minutes. After this suitable incubation period, wash solution is again introduced to dilute out the enzyme solution and to stop the action of the enzyme. This shortened wash phase is preferably a cold wash to ensure that the enzyme action is stopped as completely as possible at the moment desired by the user. Additional washes are then performed, preferably about three, to ensure that all the enzyme is removed and to preserve the stability and integrity of the final reagent product. Left-over enzyme is undesirable in that the membranes of the treated red blood cells could be destroyed over time.

The thus treated portion of the blood product is then expressed out into a second clean holding container (not pictured) through a separation line, and diluted with a suitable buffer for optimal packaging concentrations for final reagent product containing untreated and treated red blood cells (such as Resolve Panel C® as referred to above).

The following examples provide more specific embodiments of the present invention, but are not to be considered limitative thereof:

EXAMPLE I

The COBE 2991 Blood Cell Processor is manually programmed as follows:

The COBE 2991 Blood Cell Processor is set up for washing of a blood product unit as follows:

A. Dials

Timer 1=3 minutes
Timer 2=2 minutes
Centrifuge Speed=3,000 rpm
"Superout" rate=450 ml/min
Minimum Agitate Time=60 seconds
Superout volume=600 ml
Valve Selector=V2

B. PINS (manual programming of cell processor)

| Timer | Stop PC (packed cells) | Valve 1 2 3 | Stop RC (resuspended cells) | Red Cell Overide |
|---|---|---|---|---|
| 0 | | | 0 | 0 |
| | 0 | | 0 | 0 |
| | 0 | | 0 | |
| | 0 | | 0 | 0 |

After the device is programmed as described above, the start/spin button is pushed. The stop button is pushed when the alarm sounds.

The cells are then divided. The device is then programmed as follows for separation of the blood product unit:

| Timer | | Stop PC | Valve | | | Stop RCO |
|---|---|---|---|---|---|---|
| 1 | 2 | | 1 | 2 | 3 | |
| 0 | | | | 0 | | 0 |
| | 0 | | | 0 | | |
| | 0 | | | 0 | | |
| | 0 | | | 0 | | |
| | 0 | | | 0 | | |

Spin Timer 1=15 seconds
Spin Timer 2=2 minutes
Centrifuge Speed=500 RPM
Minimum Agitate Time=60
Superout Volume=350 ml The blood product unit is agitated immediately before separation (next step) to avoid settling of the red blood cells.

The ficin, stored as a frozen concentrated stock solution in phosphate buffered saline is diluted with ORS® to approximately a 0.07% solution. The PIN setting in Section B above ensures that excess phosphate buffered saline solution removed. This solution is then added to the separated cells. The device is then programmed as follows:

| Timer | | Stop PC | Valve | | | Stop RCO |
|---|---|---|---|---|---|---|
| 1 | 2 | | 1 | 2 | 3 | |
| 0 | | | 0 | | | |
| | 0 | | | 0 | | |
| | 0 | | | 0 | | |
| | 0 | | | 0 | | |
| | 0 | . | | 0 | | 0 |
| | 0 | | | 0 | | |

Spin Timer 1=2 minutes
Spin Timer 2=2 minutes
Centrifuge Speed=3,000 RPM
Minimum Agitate Time=100
Superout Volume=600 ml The ficin is allowed to enter the system for approximately 5 to 7 minutes and allowed to agitate with the red cells for approximately 80 seconds. Alternatively, following the first wash, the agitate time can be set back to 60 seconds.

The step/reset button is depressed when the alarm sounds. The device is then programmed as follows:

|  Timer  |    | Stop |    | Valve |    |    |          |
| --- | --- | --- | --- | --- | --- | --- | --- |
| 1 | 2 | PC | 1 | 2 | 3 | RC | Stop RCO |
| 0 |   |    | 0 |   |   |    |          |
|   | 0 |    |   | 0 |   |    |          |
|   | 0 |    |   | 0 |   |    |          |
|   | 0 |    |   |   | 0 |    | 0        |

Spin Timer 1=15 seconds
Spin Timer 2=15 seconds
Centrifuge Speed=500 rpm
Minimum Agitate Time=30 seconds
Superout Volume=600 ml
Superout Rate=450 ml/minute
Auto/Manual=AUTO The start/spin button is then pushed. The stop button is pushed when the alarm sounds. The treated cells are then removed from the device.

EXAMPLE II

Preparation of IgG Coated Latex Particles

A Cell Processor is used in the preparation of coated latex particles. PIN settings are adjusted to carry out the following steps:

Add approximately 240 ml of a 2.5% suspension of 3 u Latex-COOH particles (Polysciences of Warrington, Pa.) to the cell processor. Centrifuge and remove the supernatant. Wash two times with a carbonate buffer solution, pH 9.5, and three times with a phosphate buffer solution, pH 4.5. Resuspend the latex with agitation with the phosphate buffer and add 1-(3-Dimethylaminopropyl)-3 ethyl carbodiimide hydrochloride (ECDI) so that the final mixture in the cell processor is approximately 1% latex and 1% ECDI. Agitate for approximately three hours. Wash three times with borate buffer solution, pH 8.5. Resuspend the latex in the borate buffer and add 320 ug/ml anti-IgG. Agitate intermittently overnight. (Alternately superout the mixture and stir overnight. Add back to the cell processor after stirring.) Centrifuge the latex suspension and remove the supernatant. Resuspend the latex in the borate buffer to approximately 1% suspension. Block with BSA. Add the BSA to the latex suspension and agitate for approximately twenty minutes. Remove the supernatant and repeat blocking with BSA. Centrifuge and resuspend to an approximate 2.5% latex suspension in the final resuspension buffer. Remove from the cell processor to a bulk container.

EXAMPLE III

Glycerol is used as a cryopreservative agent in preparing red cells for freezing. The COBE 2991 cell processor is used as an aid in this process, by monitoring the amount and speed of addition of the glycerol. Rapid introduction of glycerol can cause damage to the red cell, resulting in hemolysis after thawing.

Blood is allowed to enter the centrifuge bowl of the cell processor. Red cells are separated from the plasma by centrifuging at approximately 3000 rpm for 3 to 5 minutes. As much plasma as possible is expressed into the waste bag. While agitating, add 100 ml of 6.2M glycerol to the packed cells. Allow to equilibrate for 5 minutes, then add approximately 300 ml more of glycerol, with agitation. Final concentration should be 40% weight to volume. If desired, extracellular glycerol may be removed by centrifugation. Remove blood/glycerol solution to a freezing bag, label, and place in a −65° C. or below freezer.

Pin and dial settings are changed and set as appropriate for this application.

What is claimed:

1. A method for treating a red blood cell dispersion using an automated blood cell processor, comprising adjusting said blood cell processor to contact all or a portion of said dispersion with a proteolytic enzyme solution at ambient temperature, in a concentration sufficient to modify at least a portion of the surface of all or a portion of said dispersion and for a period of time from about 1 minute to about 30 minutes.

2. The method of claim 1 wherein the proteolytic enzyme solution is a ficin solution.

3. The method of claim 2 wherein the ficin solution is at a concentration between about 0.02% and about 0.25%.

4. The method of claim 3 wherein the ficin solution is at a concentration between about 0.05% and about 0.1%.

5. A method for treating red blood cells using an automated blood cell processor, comprising adjusting said blood cell processor to contact all or a portion of said red blood cells with a ficin solution at ambient temperature, at a concentration between about 0.02% and 0.25% of ficin, for a period of time of about 60 seconds to about 30 minutes, to modify at least a portion of the surface of all or a portion of said red blood cells.

6. The method of claim 5 wherein the ficin concentration is about 0.05% to about 0.1%, and wherein the period of time is about 5 minutes to about 7 minutes.

* * * * *